United States Patent [19]

Laks

[11] Patent Number: 4,906,656
[45] Date of Patent: Mar. 6, 1990

[54] BIOCIDAL TREATMENT OF MATERIALS WITH CATECHINS

[75] Inventor: Peter E. Laks, Hancock, Mich.

[73] Assignee: Board of Control of Michigan Technological University, Houghton, Mich.

[21] Appl. No.: 155,299

[22] Filed: Feb. 12, 1988

Related U.S. Application Data

[62] Division of Ser. No. 907,477, Sep. 15, 1986, Pat. No. 4,760,088.

[51] Int. Cl.$^4$ ............................................. A01N 43/16
[52] U.S. Cl. .................................................. 514/456
[58] Field of Search ............................... 514/456, 337

[56] References Cited

U.S. PATENT DOCUMENTS

| | | | |
|---|---|---|---|
| 3,270,003 | 8/1966 | Van Blaricom et al. | 260/236.5 |
| 3,888,990 | 6/1975 | Courbat et al. | 424/283 |
| 3,928,585 | 12/1975 | Cervelle | 424/195 |
| 4,166,861 | 9/1979 | Bonait et al. | 424/278 |
| 4,248,789 | 2/1981 | Okada | 260/345.2 |
| 4,460,578 | 7/1984 | Cervelle et al. | 424/195 |

OTHER PUBLICATIONS

The condensed chemical dictionary, 9th ed., Van Nostrand Reinhold Co., New York, 1977, page 108.
Thompson et al., JCS, Perkin I (11), 1387-99 (1972).

*Primary Examiner*—Nicky Chan
*Attorney, Agent, or Firm*—Michael, Best & Friedrich

[57] ABSTRACT

Sulfide derivatives of catechins derived from condensed tannins have broad spectrum biocidal characteristics. Epicatechin-4-alkylsulfides and cupric complexes thereof containing up to 20, preferably 5 to 15, carbon atoms are particularly effective biocides against wood rotting fungi and gram-positive bacteria.

Such sulfides are prepared by reacting condensed tannin, either in the form of a purified tannin extract or comminuted plant tissue, with an appropriate thiol under mild acidic conditions.

13 Claims, No Drawings

BIOCIDAL TREATMENT OF MATERIALS WITH CATECHINS

This is a division of application Ser. No. 907,477, filed Sept. 15, 1986, now U.S. Pat. No. 4,760,088.

BACKGROUND OF THE INVENTION

This invention relates to derivatives of catechins and methods for preparing same. In one aspect, the invention relates to biocidal compositions including sulfide derivatives of catechins, particularly epicatechins, derived from condensed tannin as the active ingredient.

Catechin, epicatechin and certain derivatives of catechin and epicatechin are known to possess pharmaceutical and/or viricidal properties. For example, U.S. Pat. No. 4,460,578 discloses that the extract from *Hedysarum fructescens willd* consisting of a combination of flavonoids, catechin, tannins and phenol acids is effective for the treatment of tegumentary virus infections. U.S. Pat. No. 4,248,789 discloses that catechins derived from tannin extracted from tea leaves have a viricidal effect. U.S. Pat. No. 4,166,861 discloses that epicatechin and ketal and esters of catechin and epicatechin have a choleretic, hypocholesterolimic, hypolipaemic and hepatoprotective effect. U.S. Pat. No. 3,888,990 discloses that sulfonic acid derivatives of epicatechin are effective in the treatment of vascular diseases and conjunctive tissue disorders. Examples of other flavonoid extracts are disclosed in U.S. Pat. Nos. 3,928,585 and 3,270,003.

Applicant has found that sulfide derivatives of catechins, particularly epicatechins, derived from condensed tannin have biocidal characteristics.

— SUMMARY OF THE INVENTION

An object of the invention is to provide novel sulfide derivatives of catechins derived from condensed tannins and a method for preparing same.

Another object of the invention is to provide sulfide derivatives of catechins derived from condensed tannins having biocidal characteristics.

Another object of the invention is to provide cupric complexed sulfide derivatives of catechins derived from condensed tannins.

Other objects, aspects, and advantages of the invention will become apparent to those skilled in the art upon reviewing the following detailed description and the appended claims.

The invention provides broad spectrum biocidal compositions comprising a biocidally effect amount of a sulfide derivative of a catechin, preferably epicatechin, derived from condensed tannin and a biocidally acceptable diluent or carrier.

In one embodiment, such thiol derivatives are represented by the formula:

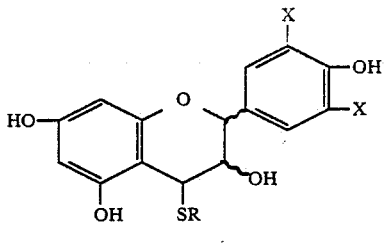

wherein
X=H or OH, and
R=alkyl, aryl, aralkyl, aralkenyl, or heterocylic group.

The invention also provides cupric complexed sulfide derivatives of catechins derived from tannin.

The invention also provides novel alkyl sulfide derivatives containing up to 20 carbon atoms which can be prepared by reacting purified condensed tannin derived from the bark or other tissues of a coniferous tree or communited bark or other tissue from such trees with a thiol having the formula RSH under mildly acidic conditions.

DESCRIPTION OF THE PREFERRED EMBODIMENTS

As used herein, the term "catechin(s)" means catechin, epicatechin, gallocatechin, epigallocatechin and 3, 4', 5, 7-tetrahydroxyflavan derived from condensed tannins. Epicatechin is the preferred catechin for use as the active ingredient in a biocidal composition.

The tannins used as the starting material are condensed tannins of the procyanidin class. These tannins are present in a wide variety of plant tissue. Higher concentrations are found in the bark and other tissues of most commercially important North American conifers, such as southern pine, other pines, Douglas fir, and the hemlocks, as well as nut shells and skins and other agricultural by-products.

The starting material can be (1) a purified or semi-purified, condensed tannin extracted from the bark or other plant tissue or (2) a comminuted or powdered bark or other plant tissue. In either case, the starting material is combined with a thiol having the formula RSH (wherein R is as defined below) and an organic solvent having appropriate solubilization characteristics. The resulting mixture is reacted in the presence of a small amount of a mild acid at an elevated temperature to depolymerize the condensed tannin to produce cleavage/addition products of condensed tannin of the procyanidin class.

The R in the thiol and formula I can be an alkyl or a substituted alkyl group, aryl or substituted aryl group, aralkyl or substituted aralkyl group, aralkenyl or substituted aralkenyl group or a heterocyclic group.

The alkyl group can be straight chained, branched or cyclic. The aryl groups and the aryl constitutent of the aralkyl and aralkenyl groups can be substituted. The heterocyclic group can be oxygen-, sulfur- on nitrogen-containing heterocyclic groups such as furyl, thiophenyl or pyridyl.

Suitable substitutents on the R groups include halogens, amines, thiols and nitro groups.

At present, substituted and unsubstituted alkyl groups are preferred with straight-chained alkyl groups containing up to 20, preferably 5 to 15, and most preferably 10, carbon atoms.

Suitable thiols include hexyl thiol, octyl thiol, decyl thiol, dodecyl thiol, hexadecyl thiol, 2-chloroethyl thiol, thiophenol, thiocresol, thiouracil and benzyl thiol.

At least a stoichiometric of thiol should be used and preferably at least a 10% molar excess of thiol is included in the reaction.

The organic solvent used as the reaction medium solubilizes the tannin and thiol but is inert to the reaction. Suitable organic solvents include ethanol, acetone and dioxane. When comminuted plant tissue is used as the starting material, the solvent preferably has the capability of extracting tannin from the tissue under the reaction conditions.

The acid acts as a catalyst in the depolymerization of tannin. A sufficient amount of the acid is added to make the reaction medium mildly acidic. The acid used should be soluble in the solvent used and easily separable from the reaction mixture during the purification process. Suitable acids include acetic acid, other carboxylic acids, p-toluenesulfonic acid, sulfuric acid and hydrochloric acid. Acetic acid, for example 1% acetic acid in ethanol, is preferred because of its appropriate acid strength, miscibility with organic solvents and volatility.

The reaction is carried out at temperature within a range of about 25° to about 200° C., preferably about 100° to about 125° C., in a sealed, pressure-tight reaction vessel, for example, a Paar reaction bomb.

At 100° C. the reaction takes up to about 12 hours to obtain a maximum yield. The reaction rate and yield is temperature dependent, with lower and higher temperatures resulting in slower and more rapid reaction rates, respectively.

When comminuted bark or other plant tissue is used as the starting material, the reaction mixture preferably is agitated by stirring or the like and the organic solvent combined with the tissue and the thiol acts as the reaction medium and also extracts tannin from the plant tissue, thereby eliminating the necessity of first isolating the tannin from the plant tissue. Best yields and reaction rates are obtained by using very finely ground bark or other plant tissue. The crude reaction mixture is filtered to remove the solids. The filtrate is concentrated by evaporation, a small amount of water added to the filtrate and the mixture extracted with a suitable solvent, such as hexane, to remove unreacted thiol. The remaining solution can be further extracted with another suitable solvent, such a chloroform, and the desired catechin derivative goes into the solvent layer. If necessary, the crude product can be purified still further by liquid column chromatography using an appropriate packing material, such as Sephadex LH-20, and solvent, such as 95% ethanol.

When purified condensed tannin is used as a starting material, a similar procedure can be followed, except the filtration step is eliminated.

The catechin derivatives of the invention can be used as a biocide e.g., a bactericide, pesticide, or fungicide, particularly against wood-destroying fungi. An effective amount of a catechin derivative is combined with a carrier, diluent or excipient acceptable for the intended mode of administration. For example, if used as a fungicide for treating wood, an effective amount of a catechin derivative can be combined with a suitable solvent, such as ethanol, acetone or an aqueous solution of ammonium hydroxide and the resulting solution used to impregnate the wood by dipping, spraying or the like. If used as a bactericide, an effective amount of a catechin derivative is dissolved or dispersed in a suitable sterile liquid for parenteral or oral administration or combined with a suitable excipient and made into tablets or capsules for oral administration.

Cupric complexes of the sulfide derivatives of catechins of the invention can be formed in situ or as an isolatable complex. For example, if a cupric complex is to be used as a fungicide, it can be formed in situ by first saturating a wood article or other article to be treated with a solution of a sulfide derivative, such as by using alternating vacuum and pressure. The treated material is air-dried, treated with an aqueous solution of a cupric salt, such as cupric chloride or copper sulfate, and again air-dried. The concentration of the cupric salt solution is such that the molar ratio of the sulfide derivative to the copper (as $Cu^{++}$) is about 1:1. A water-insoluble cupric complex is formed within the wood structure.

To form an isolated cupric complex, a sulfide derivative of catechin of the invention is dissolved in water with a sufficient amount of sodium hydroxide, or another suitable solubilizing reagent, to obtain complete solubilization. For example, it usually takes about two moles of sodium hydroxide per mole of catechin derivative to obtain complete solubilization. An aqueous solution of a cupric salt is slowly added to the catechin derivative solution until the mole ratio of the catechin derivative to $Cu^{++}$ is about 2:1. A cupric complex forms immediately, precipitates out of solution and can be recovered by filtration or the like. To prevent oxidation of the catechin derivative, the solvents used should be deoxygenated and the complexing reaction carried out under a blanket of inert gas, such a nitrogen.

A ternary complex can be formed by adding an additional ligand which has the ability to form strong complexes with $Cu^{++}$, such as ethylene diamine or dipyridine, to the aqueous solution of a catechin derivative. Preferably, a 1:1:1 molar ratio of catechin derivative, $Cu^{++}$ and the additional ligand is used. After isolation, a suitable solvent such as ethanol, acetone or an aqueous solution of ammonium hydroxide can be used as a carrier solvent for the cupric or ternary complex, if necessary for the intended treatment.

Without further elaboration, it is believed that one skilled in the art, using the preceding description, can utilize the present invention to its fullest extent. The following examples are presented to exemplify embodiments of the invention and should not be construed as limitations thereof.

EXAMPLE 1

Different epicatechin-4-alkylsulfides were synthesized by reacting purified condensed tannin with n-hexyl thiol, n-octyl thiol, n-decyl thiol, n-dodecyl thiol and hexadecyl thiol. For each synthesis, 5 g of purified condensed tannin was combined with 5 g of one of the thiols and 1 ml of acetic acid and 100 ml of 95% ethanol in a sealed reaction container. The solution was heated to a temperature of about 105° C. for approximately 12 hours. After being cooled to room temperature, the reaction solution was evaporated to about 25 ml. Approximately 100 ml of water was added to the reaction solution and the resulting mixture was extracted with hexane. The hexane layer containing unreacted thiol was discarded. The aqueous layer was extracted with chloroform and a reasonably pure epicatechin-alkylsulfide product was obtained. This product was purified by passing through a chromatographic column using Sephadex LH-20 as the packing and 95% ethanol as the eluent. The product was identified as an epicatechin-alkylsulfide by NMR and elemental analysis.

EXAMPLE 2

Epicatechin-alkylsulfides also were prepared by using finely-ground, dry inner bark from eastern hemlock as the starting material. 200 g of the ground bark was combined with 50 g of thiol and 10 ml of acetic acid in 1500 ml of 95% ethanol in a pressurized reaction vessel equipped with a stirrer. The reaction vessel was heated to 100° C. and the reaction carried out at that temperature with the stirrer operating for 12 hours. After cooling, the reaction mixture was filtered to remove solids and the filtrate was treated in the manner described in Example 1 to obtain the desired epicatechin-alkylsulfide.

EXAMPLE 3

Tests were made to determine the biocidal properties of the epitcatechin-4-alkylsulfides prepared in Examples 1 and 2 on different wood-rotting fungi and bacteria.

Fungi

Agar plates containing the epicatechin-4-alkylsulfide to be tested were prepared by adding one part of an ethanol solution containing a known concentration of the test compound to 99 parts of molten malt extract agar. After thorough mixing, the medium was poured into 8 cm petri dishes. When the agar had cooled and hardened, the plates were inoculated by placing in the center of the plate a 5 mm diameter plug taken from an agar plate containing an actively growing culture of the test organism and incubated at 26° C. The diameter of the mycelium formed was measured when the culture on a control plate (containing no test compound) had reached the perimeter of the petri dish, or after seven days, whichever came first. Three duplicates were run for each test compound/test organism combination. The averaged results are tabulated in Table I.

TABLE I

BIOCIDAL EFFECT OF EPICATECHIN-4-ALKYLSULFIDES ON WOOD-DESTROYING FUNGI

Concentration, ppm[1]
Alkyl Substituent (R)

| Organism | $C_6$ MIC[2] | $C_6$ $LD_{50}$[3] | $C_8$ MIC | $C_8$ $LD_{50}$ | $C_{10}$ MIC | $C_{10}$ $LD_{50}$ | $C_{12}$ MIC | $C_{12}$ $LD_{50}$ | $C_{16}$ MIC | $C_{16}$ $LD_{50}$ |
|---|---|---|---|---|---|---|---|---|---|---|
| WHITE-ROTTERS | | | | | | | | | | |
| Phanerochaete chrysosporium | 250 | 50 | 100 | 25 | 50 | 8 | 1000 | 50 | 1000 | 100 |
| Pycnoporus cinnabarinus | 500 | 100 | 1000 | 10 | | | 1000 | 1000 | | |
| Coriolus versicolor | 800 | 100 | 250 | 80 | 200 | 50 | 1000 | 50 | 1000 | 1000 |
| BROWN-ROTTERS | | | | | | | | | | |
| Wolfiporia cocos | 500 | 100 | 1000 | 100 | | | 1000 | 800 | | |
| Poria placenta | 500 | 80 | 250 | 25 | 1000 | 50 | 1000 | 75 | 1000 | 1000 |
| Geophyllum trabeum | 1000 | 100 | 1000 | 100 | 1000 | 100 | 1000 | 250 | 1000 | 1000 |
| SOFT-ROTTERS | | | | | | | | | | |
| Chaetomium globosom | 500 | 80 | 1000 | 25 | | | 1000 | 50 | | |
| Scytalidium lignicola | 80 | 20 | 25 | 5 | 8 | 2 | 100 | 25 | 200 | 50 |
| Lecythophora hoffmannii | 800 | 100 | 400 | 100 | 300 | 80 | 1000 | 100 | 1000 | 1000 |

Notes:
[1]Maximum concentration tested - 1000 ppm.
[2]Minimum Inhibitory Concentration (No growth observed at this concentration).
[3]Concentration at which mycelium growth is about one half of the diameter of a copntrol culture set up at the same time.

Bacteria

Agar plates containing the test compounds were made as above, but with brain-heart infusion agar. The plates were inoculated with a standardized suspension of a bacterial cells using a calibrated 3 mm loop and incubated at 35° C. After one day (two days for *Micrococcus luteus*), the number of resulting bacteria cultures were counted. Streptomycin was used under the same conditions on each test organism for a comparison. The results are tabulated in Table II.

TABLE II

BIOCIDAL EFFECT OF EPICATECHIN-4-ALKYL SULFIDES ON BACTERIA

Concentration, ppm[1]
Alkyl Substituent (R)

| Organism | $C_6$ MIC[2] | $C_8$ MIC | $C_{10}$ MIC | $C_{12}$ MIC | $C_{16}$ MIC | Strep[3] MIC |
|---|---|---|---|---|---|---|
| GRAM-NEGATIVE BACTERIA | | | | | | |
| Klebsiella pneumoneae | 500 | 500 | 500 | 500 | 500 | 8 |
| Escherchia coli | 300 | 500 | 500 | 500 | 500 | 5 |
| Enterobacter cloacae | 300 | | 500 | | 500 | 1 |
| Pseudomonas aeruginosa | 500 | | 300 | | 50 | 50 |
| GRAM-POSITIVE BACTERIA | | | | | | |
| Streptococcus faciens | 200 | 60 | 30 | 75 | 100 | 50 |
| Bacillus cereus | 80 | 20 | 5 | 50 | 75 | 20 |
| Micrococcus liteus | 50 | 40 | 5 | 50 | 75 | 8 |

TABLE II-continued

BIOCIDAL EFFECT OF EPICATECHIN-4-ALKYL SULFIDES ON BACTERIA

| Organism | Concentration, ppm[1] Alkyl Substituent (R) | | | | | |
|---|---|---|---|---|---|---|
| | $C_6$ MIC[2] | $C_8$ MIC | $C_{10}$ MIC | $C_{12}$ MIC | $C_{16}$ MIC | Strep[3] MIC |
| Staphylococcus aureus | 80 | 50 | 40 | 50 | 250 | 80 |

Notes:
[1]Maximum concentration tested - 500 ppm.
[2]Minimum Inhibitory Concentration (No colonies observed at this concentration).
[3]Streptomycin From these test results, it can be seen that epicatechin-4-alkylsulfides (particularly the octyl($C_8$) and decyl($C_{10}$) alkyls) are an effective fungicide against a variety of fungi. It also can be seen that epicatechin-4-alkylsulfides are effective bactericides, particularly against gram-positive bacteria. The decyl($C_{10}$) alkyl was substantially more effective against gram-positive bacteria than streptomycin. Epicatechin itself was tested and found to have no fungicidal and minimal bactericidal properties at the concentrations tested.

The catechin derivatives of the invention can be used for large number of applications including food preservatives, sanitizers, metal working fluids, paints, petroleum protection, plastics and resins, agricultural fungicides and as wood preservatives. Although highly valuable, they can be produced from low cost plant tissue, for example, conifer bark which is an inexpensive, underutilized residue in the forestry industry. The condensed tannin used as the starting material can be isolated from the plant tissue by an inexpensive extraction process or extracted from comminuted plant tissue as part of the depolymerization reaction.

From the foregoing description, one skilled in the art can easily ascertain the essential characteristics of the invention and, without departing from the spirit and scope thereof, make various changes and modifications to adapt it to various usages.

I claim:

1. A method for protecting a material against the attack by microorganisms comprising applying to said material an effective amount of a biocidal composition including a compound represented by the formula

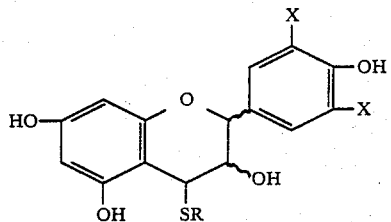

wherein
X=H or OH, and
R=alkyl, aryl, aralkyl, or aralkenyl.

2. A method according to claim 1 wherein said compound is a derivative of epicatechin.

3. A method according to claim 2 wherein such compound is complexed with $Cu^{++}$.

4. A method according to claim 2 wherein said compound is complexed with $Cu^{++}$ and another ligand.

5. A method according to claim 2 wherein said compound is a derivative of epicatechin and R is a straight-chained alkyl group.

6. A method according to claim 5 wherein R contains up to 20 carbon atoms.

7. A method according to claim 6 wherein R contains 5 to 15 carbon atoms.

8. A method according to claim 7 wherein R contains 10 atom atoms.

9. A method according to claim 1 wherein R is a straight-chained alkyl group.

10. A method according to claim 9 wherein R contains up to 20 carbon atoms.

11. A method according to claim 10 wherein R contains 5 to 15 carbon atoms.

12. A method according to claim 11 wherein R contains 10 carbon atoms.

13. A method according to claim 1 wherein said microorganism is a wood-rotting fungi.

* * * * *